(12) United States Patent
Campisi et al.

(10) Patent No.: US 9,789,200 B2
(45) Date of Patent: Oct. 17, 2017

(54) THERAPEUTIC USE OF NEW PHARMACEUTICAL PREPARATIONS CONTAINING ANTITUMORAL DRUGS BOUND TO HYALURONIC ACID IN THE TREATMENT OF NEOPLASIAS

(75) Inventors: Monica Campisi, Abano Terme (IT); Davide Renier, Abano Terme (IT); Pasquale Pierimarchi, Abano Terme (IT); Annalucia Serafino, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 0 days.

(21) Appl. No.: 12/988,630

(22) PCT Filed: Apr. 21, 2009

(86) PCT No.: PCT/IB2009/005309
§ 371 (c)(1),
(2), (4) Date: Dec. 27, 2010

(87) PCT Pub. No.: WO2009/130564
PCT Pub. Date: Oct. 29, 2009

(65) Prior Publication Data
US 2011/0189265 A1    Aug. 4, 2011

(30) Foreign Application Priority Data

Apr. 22, 2008 (IT) .................................. PD08A0125
Oct. 8, 2008 (IT) .................................. PD08A0283

(51) Int. Cl.
*A61K 47/48* (2006.01)
(52) U.S. Cl.
CPC ................................ *A61K 47/4823* (2013.01)
(58) Field of Classification Search
None
See application file for complete search history.

(56) References Cited

U.S. PATENT DOCUMENTS

2004/0234497 A1* 11/2004 Luo et al. .................... 424/85.1

FOREIGN PATENT DOCUMENTS

| EP | 1 080 732 A1 | 3/2001 |
| WO | WO-2004/035629 A2 | 4/2004 |
| WO | WO-2006042146 A2 | 4/2006 |
| WO | WO-2007/014784 A2 | 2/2007 |
| WO | WO-2008012365 A2 | 1/2008 |

OTHER PUBLICATIONS

PubMed abstract of Maeda et al "Antitumor activity of new series of platinum complexes . . . " Anticancer Drugs (1993) vol. 4, No. 2, pp. 167-171.*
Cai, S. et al "Intralymphatic chemotherapy using a hyaluronan-cisplatin conjugate" J. Surg. Res. (2008) vol. 147, pp. 247-252.*
Maeda, M. et al "Antitumor activity of a new series of platinum complexes . . . " Anti-Caner Drugs (1993) vol. 4, pp. 167-171.*
Jeong, Y. et al "Cisplatin-incorporated hyaluronic acid . . . " J. Pharm. Sci. (2008) vol. 97, No. 3, pp. 1268-1276.*
Jun, Y. et al "Selective tumor targeting by enhanced permeability . . . " J. Inorg. Biochem. (2005) vol. 99, pp. 1593-1601.*
Gianasi, E. et al "HPMA copolymers platinates . . . " J. Drug Targeting (2002) vol. 10, No. 7, pp. 549-556.*
Burke, T. and V. Adams (eds.) Camptothecins in Cancer Therapy. Springer, 2005 (Burke, T. et al "Recent advance in camptothecin drug design . . . " Chapter 8, pp. 171-190).*
Greenwald, R. et al "Effective drug delivery by PEGylated drug conjugates" Adv. Drug Deliv. Rev. (2003) vol. 55, pp. 217-250.*
D'Addona, D. et al "Preparation of carbamates from amines . . . " Tet. Lett. (2001) vol. 42, pp. 5227-5229.*
Day, A. et al "Hyaluronan binding proteins . . . " J. Biol. Chem. (2002) vol. 277, No. 7, pp. 4585-4588.*
Auzenne, E. et al "Hyaluronic acid-paclitaxel . . . " Neoplasia (2007) vol. 9, No. 6, pp. 479-486.*
International Preliminary Report on Patentability for PCT/IB2009/005309 dated Jul. 16, 2010.
International Search Report for PCT/IB2009/005309 dated Sep. 1, 2009.

(Continued)

*Primary Examiner* — Leigh C Maier
(74) *Attorney, Agent, or Firm* — Birch, Stewart, Kolasch & Birch, LLP

(57) ABSTRACT

The present invention describes the new use in the oncologic field of bioconjugates as differentiating agents obtained by the conjugation between hyaluronic acid (HA) and a chemotherapeutic product (identified hereafter with the tradename ONCOFID®) among which, in particular, Irinotecan, Doxorubicin, Paclitaxel, Cis-platinum and 5-Fluorouracyl (5-FU) for treating primary tumors and metastasis. In particular, the biological behavior is described in terms of action mechanism, efficacy and tolerability of pharmaceutical preparations of derivative of ONCOFID® soluble in water. More specifically, the invention relates to the surprising biological and pharmacological effect demonstrated by formulations based on ONCOFID-S (HA-SN38 conjugates) and ONCOFID-D (HA-Doxorubicin conjugates) in promoting the differentiation of tumoral cells towards a untransformed phenotype, compared with the reference drug Irinotecan (or CPT11 whose active form is represented by SN38) and Doxorubicin.

20 Claims, 10 Drawing Sheets

(56) References Cited

OTHER PUBLICATIONS

Li, H et al. "Synthesis and Biological Evaluation of a Cross-Linked Hyaluronan-Mitomycin C Hydrogel" Biomacromolecules. Jan. 30, 2004; vol. 5 pp. 895-902.
Akima, K et al. "Evaluation of Antitumor Activities of Hyaluronate Binding Antitumor Drugs: Synthesis, Characterization and Antitumor Activity" Journal of Drug Targeting. 1996; vol. 4 pp. 1-8.
Brewster, M. E. et al. "Verious Cyclodextrin Derivatives Enhance Solution Stability and Dissolution Rate of Doxorubicin Hydrocloride" Pharmatec Incorporated, Center for drug Discovery at University of Florida, Department of Pharmacy at University of Iceland. 1992; pp. 442-447.

\* cited by examiner

48h Treatment
Cytokeratin 20 — SEM control / Hyaluronic Acid / Oncofid-S 1 μM

HIRID Batch RS025/06 SN38 3,26%

% Survived cells vs control

Fig. 7
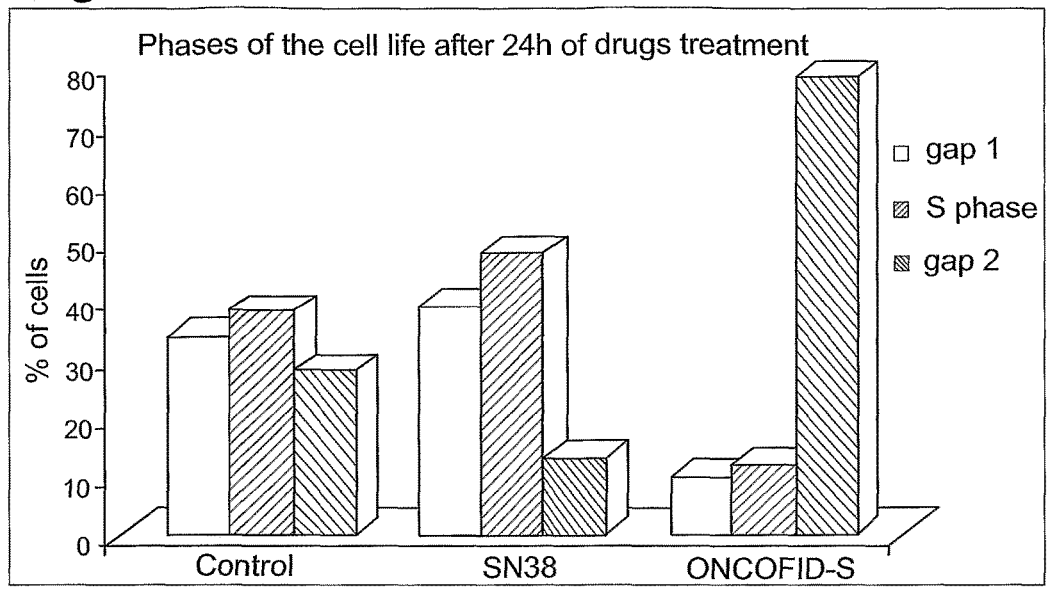
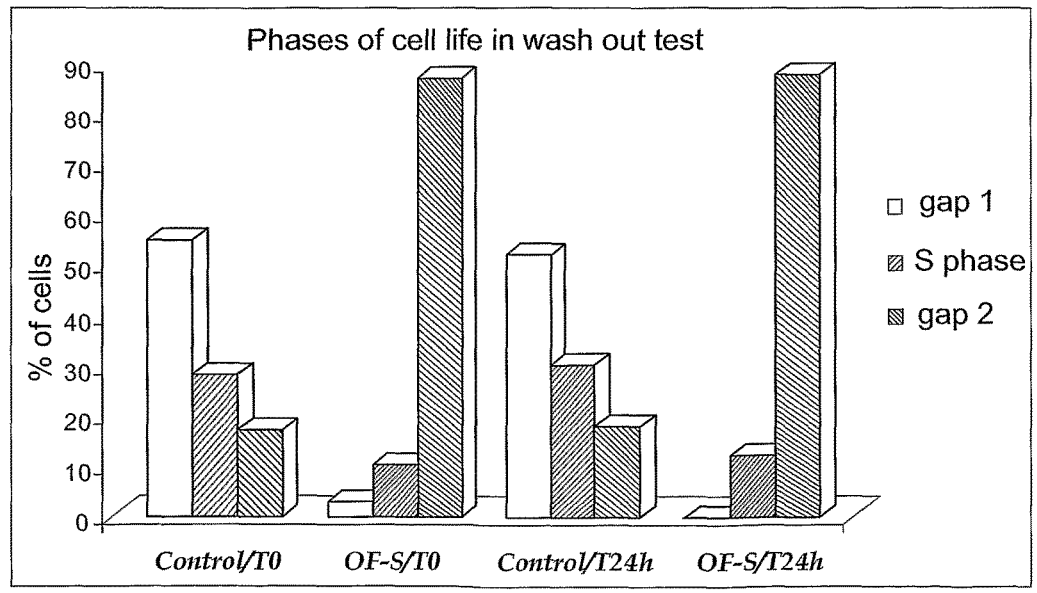
Fig. 8

THERAPEUTIC USE OF NEW PHARMACEUTICAL PREPARATIONS CONTAINING ANTITUMORAL DRUGS BOUND TO HYALURONIC ACID IN THE TREATMENT OF NEOPLASIAS

This Application is the National Phase Under 35 U.S.C. §371 of PCT International Application No. PCT/IB2009/005309, which has an International filing, date of Apr. 21, 2009, and claims priority to two Italian patent applications. Italian Patent Application No. PD2008A 000125 filed on Apr. 22, 2008 and Italian Patent Application No. PD2008A 000283 filed on Oct. 8, 2008. The entire contents of all applications listed above are hereby incorporated by reference.

OBJECT OF THE INVENTION

The present invention describes the new use in the oncologic field of bioconjugates as differentiating agents obtained by the conjugation between hyaluronic acid (HA) and a chemotherapeutic product (identified hereafter with the trade-name ONCOFID®) among which, in particular, Irinotecan, Doxorubicin, Paclitaxel, Cis-platinum and 5-Fluorouracyl(5-FU) for treating primary tumors and metastasis. In particular, the biological behaviour is described in terms of action mechanism, efficacy and tolerability of pharmaceutical preparations of derivative of ONCOFID® soluble in water.

More specifically, the invention relates to the surprising biological and pharmacological effect demonstrated by formulations based on ONCOFID-S (HA-SN38 conjugates) and ONCOFID-D (HA-Doxorubicin conjugates) in promoting the differentiation of tumoral cells towards a untransformed phenotype, compared with the reference drug Irinotecan (or CPT11 whose active form is represented by SN38) and Doxorubicin.

FIELD OF THE INVENTION

In recent years, the progressive knowledge of vital processes which determine the start, development, dispersion and implanting of a tumour and its metastases has not only offered researchers the possibility of studying, synthesizing and/or testing new chemical molecules as new antitumoral agents, but has also facilitated the study and perfectioning of new treatment therapies which allow problems linked to the toxicity of antineoplastic drugs to be overcome. Numerous drugs with an antitumoral activity, in fact, generally have a series of negative characteristics such as:

- low solubility in water, as many molecules are hydrophobic substances which are difficult to administer;
- low selectivity towards tumoral cells, with a consequent toxicity towards non-carcinogenic cells;
- multiple undesired effects on a systemic level;
- low plasmatic half-life, with the consequent necessity for repeated administrations;
- induction of resistance to chemotherapeutic treatment in the tumor.

In addition to searching for increasingly more effective new active principles in oncologic therapy, the scientific field is parallelly trying to exploit to the utmost molecules whose antiballistic activity is already known, improving their performances and attempting to reduce the negative characteristics, as described above.

One of the most widely-used strategies for reducing the intrinsic toxicity of antitumoral drugs is linked to the possibility of guiding the active principle directly and selectively to the tumoral cell.

A promising approach is offered by the chemical conjugation of the antitumoral drug to groups provided with active targeting which, by specifically interacting with the receptorial sites of the neoplastic cell, guarantee a high selectivity of the drug in tumoral tissues. A different approach is represented by the bond with macromolecules (i.e. polymers) which, by conferring a high molecular weight, allow a greater accumulation of the active principle in neoplasias due to the EPR effect (Enhanced Retention and Permeation), i.e. an accumulation linked to the passage through the fenestrated epithelium of the vessels that supply the tumor (passive targeting) inadequately drained by the lymphatic system.

Since many years, many antitumoral drugs used in the oncologic field were chemically modified to obtain prodrugs, therapeutically inactive derivatives which only become active in vivo, thanks to spontaneous hydrolysis processes and/or enzymatic degradations which lead to the release of the active principle, thus increasing its therapeutic efficacy.

The solubility of chemotherapeutic drugs in the circulatory system represents the essential condition for their pharmacological effect. Some drugs, in fact, which have proved to be extremely active in various types of tumours such as, for example, Camptothecins, Paclitaxel and alkaloids deriving from Vinca, due to their high insolubility have problems of intravenous administration (and, for hormones and anti-hormones, also intramuscular) which can limit and restrict their clinical application.

For the above reasons, new chemotherapeutic drugs have been synthesized, which are created by the chemical bond (direct or indirect by means of a spacer) between the classical drug and so-called "therapeutic polymers" which, in addition to conferring important physico-chemical characteristics to the active principle (such as greater solubility), are capable of giving it an active and/or passive targeting, increasing its efficacy. These therapeutic polymers can in fact act as a carrier for the drug, or they can also exert an intrinsic biological activity.

Among these polymers, the use of hyaluronic acid (HA) has proved to be extremely promising, whose favourable characteristics make it an adequate carrier for the administration of anti-neoplastic agents.

The new bioconjugates of HA and antitumoral drugs identified with the trade-name of ONCOFID®, known in the state of the art (WO2004/035629 e WO2007/014784), claim the following characteristics:

- overcoming the problem relating to the intrinsic toxicity of the drug in that it is directly guided to the tumoral cell, as many tumoral phenotypes over-express the receptor CD-44 specific for HA on their surface;
- increase in the solubility, as it has been demonstrated that the bond of liposoluble drugs to strongly hydrophilic molecules such as HA, considerably increases the solubility of the drug itself in the circulatory system;
- overcoming the problem of resistance induced by classical antitumoral drugs;
- new physico-chemical characteristics (such as for example an increase in the stability of the drug and therefore an increase in its permanence in the tumoral site).

SN-38 is the active metabolite of Irinotecan, a pharmacological derivative of Camptothecin, whose use relates to the treatment of various types of tumours such as melanomas, breast cancer, ovarian tumours, gastric, lung, brain, pancreatic tumours and colon-rectal cancer. This drug has a high antitumoral activity but it cannot be administered as such as it is being not soluble in water and, for this reason, has been chemically conjugated with HA.

Colon-rectal tumours are one of the most aggressive forms of tumour and represent one of the most frequent causes of death by neoplasia in Western countries.

The formation of cancer in the colon-rectum is due to the uncontrolled proliferation of cells of the mucosa which lines this organ, its etiology is still unknown even if epidemiological studies have identified possible risk factors, such as:
- food habits
- genetic factors
- neoplastic polyps
- intestinal inflammatory diseases.

It is known that one of the prognostic biological factors of the carcinoma and adenoma of the colon-rectum is the APC (Adenomatous Polyposis Coli) gene. Held responsible for familial colic polyposis, somatic mutations of this gene represent the first event in the natural history of adenomas and carcinomas of the colon.

Under normal conditions (in the absence of neoplasias), the APC gene is localized on the chromosome 5 and encodes a cytoplasmatic protein (APC protein) which plays a key role in the regulation of the apoptosis of the cell cycle, inter-cellular interaction and adhesion, migration processes in addition to the metastatization of tumours. The most well-known function of the APC protein is its association with the GSK-3β protein (glycogen-synthetase kinase 3 β protein) for the regulation of the quantity of free β-catenin present in the cytoplasm and therefore in the nucleus: the above proteins, in fact, by phosphorylating the free β-catenin on a cytoplasmatic level, promotes its degradation. β-catenin is a protein capable of binding itself to the cytoplasmatic domain of a membrane protein, E-cadherin, involved in the cellular adhesion process. The destruction of the E-cadherin-β-catenin intracellular complex (an event associated with the conversion of a non-tumoral cell into a neoplastic cell), causes the loss of the inter-cellular adhesion capacity and therefore facilitates the formation of metastases. There are many scientific demonstrations which indicate how this process takes place in both the first phases and in the progression of different neoplasias, such as in breast cancer, cancer of the skin (in particular melanomas), bone cancer, brain and thyroid cancer and in head and neck tumours, tumours of the lymphatic system, lung cancer and in cancer of the mesothelium, oesophagus, stomach, colon, colon-rectum, pancreas, liver, kidneys, ureters and bladder, prostate, endometrium and ovaries (with all the other abdominal organs). As evidence of this affirmation, experiments effected for the recovery of normal synthesis/pressure of E-cadherin in tumoral cellular lines, have demonstrated the reversion of the malign tumoral form vs an untransformed phenotype, therefore no longer neoplastic (Birchmeier W. et al., Biochim Biophys Acta, 1994, 1198(1):11-26; De Vita V. et al., CANCER, 6th Edition, 2001, Chapter 8).

In many carcinomas, a mutation in the APC gene causes the formation of an anomalous, inactive APC protein, incapable of binding to the GSK-3β protein and therefore regulating the β-catenin which therefore migrates from the cytoplasm into the nucleus where it accumulates and forms complexes with transcription factors (such as Tcf-4) acting as co-activator of oncogenes growth activators and cellular proliferation (c-MYC, cyclin D1), in addition to extracellular proteases (MMP7), which facilitate invasion processes and metastases (see FIG. 1). FIG. 1 shows a scheme of the β-catenin regulation in a normal cell (right) and in a tumoral cell (left).

β-catenin therefore has all the characteristics of an onco-protein, whereas the complex APC/GSK-3β, due to its capacity of regulating the activity of β-catenin, is defined as onco-suppressor (Kollings F. et al, Digestion, 2002, 66:131-144). The rapid downregulation of the β-catenin accumulated in the nucleus is in fact obtained thanks to the action of APC (when not mutated) and GSK-3β proteins which when moving into the nucleus bind the onco-protein degrading it and/or transporting it again to a cytoplasmatic level where it is phosphorylated, then degraded (Neufeld K. et al., EMBO reports, 2000, 1, 6:519-523). This process is absent in tumoral cells where the APC/GSK-3β complex is inactive, therefore, the non-regulation of the nuclear quantity and activity of β-catenin are events of primary importance in the development and metastatization of malignant neoplasias.

Chemotherapy has a fundamental role in the treatment of tumours. In managing patients affected by carcinomas of the colon-rectum, in the metastatic phase, various therapeutic procedures have been adopted: systemic chemotherapy, loco-regional chemotherapy, ablative therapies and surgery.

Chemotherapeutic treatment represents the fulcrum of therapeutic possibilities available to this group of patients. The objective response percentages obtained with chemotherapy are equal to 20% with a short response duration and a low percentage of complete responses (only 5%); stabilizations of the illness represent about 30-40%.

For over 40 years 5-FU was the only therapeutic weapon available in carcinomas of the colon-rectum in the advanced phase.

In recent years new drugs have been studied associated with or without 5-FU in an attempt to improve the survival of patients affected by metastatic adenomas and carcinomas of the colon-rectum. Among these Irinotecan and Oxaliplatinum play an fundamental role. Irinotecan associated with 5-FU, has recently shown greater objective response percentages and progression time with respect to patients treated with 5-FU alone with an overall survival of about 17 months.

Irinotecan, also known as CPT-11, is available in the form of hydrochloride, it acts by forming a ternary drug-DNA-topoisomerase I complex, an enzyme which converts a super-enveloped DNA molecule into one without torsional tension in DNA transcription or replication operations. The formation of the ternary complex with the above camptothecin creates a stabilization in the system in the shear phase of the DNA and ensures that the cell is no longer able to duplicate itself causing death by apoptosis.

Irinotecan is in itself inactive, but the hydrolysis in vivo of the carbamic bond, leads to the release of the active metabolite SN38 (FIG. 2) which is the real drug responsible for the cytotoxic action, but which, as it is insoluble in water, requires particular expedients for its administration. FIG. 2 shows the chemical structure of Irinotecan® and SN38, respectively.

In the present invention, the Applicant describes the new biological and pharmacological behaviour of the conjugates of HA-antitumoral drugs identified with the trade-name ONCOFID® described in WO2004/035629 and WO2007/014784, as it is substantially different from that shown by the non-conjugated reference drugs in that it comprises new therapeutic and pharmaco-dynamic characteristics.

The present invention therefore describes and claims the surprising and unexpected biological and pharmacological effect obtained from formulations based on ONCOFID® in promoting an antiproliferative therapeutic action (therefore antitumoral) due to the differentiation/reversion of the tumoral cells towards an untransformed phenotype, rather than the induction of apoptosis.

BRIEF DESCRIPTION OF THE DRAWINGS

FIG. 7 depicts a graph showing the results obtained for the phases of the cell life after 24h of treatment.

FIG. 8 depicts a graph showing the results obtained for the phases of the cell life in a wash out test.

DETAILED DESCRIPTION OF THE INVENTION

Figure 1:
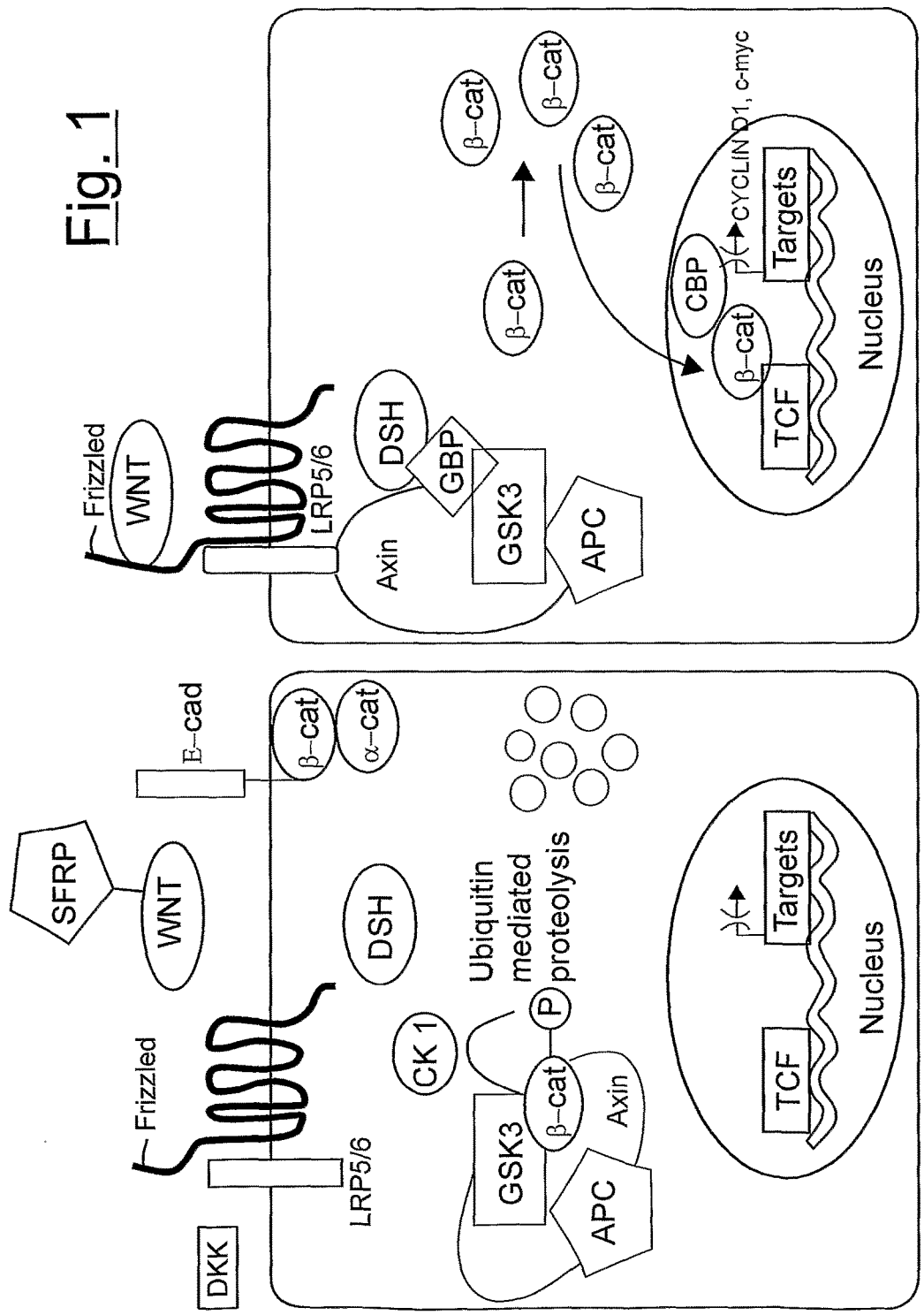
FIG. 1 depicts a scheme of the β-catenin regulation in a normal cell (right) and in a tumoral cell (left).
Figure 2:
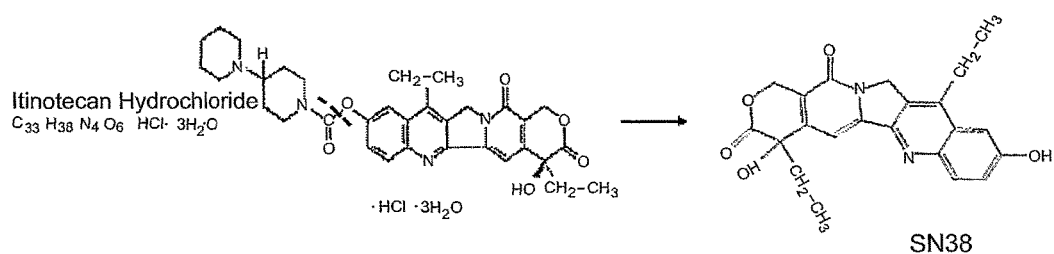
FIG. 2 depicts the chemical structure of Irinotecan® and SN38, respectively.

It is known that derivatives of ONCOFID®, as previously specified, confer advantageous characteristics to antitumoral drugs, such as solubility in water, stability, selectivity with respect to tumoral tissues, reduction in resistance to chemotherapy and potentiation of the pharmacological efficacy.

It is known that one of the most widely-spread mortal tumours is represented by colon-rectal carcinomas or adenomas and that one of the most effective therapies in the treatment of this neoplasia is that based on CPT-11 intraperitoneally. As indicated above, it is known that in this type of tumour, the mutation/inactivation of the APC gene leads to a series of events which lead to the nuclear accumulation of β-catenin and therefore the activation of transcription factors which facilitate cellular invasion and metastases.

The present invention describes and claims the new therapeutic use in the oncologic field of new formulations based on ONCOFID®, in particular ONCOFID-S represented by the HA-SN38 bioconjugate and ONCOFID-D represented by the HA-Doxorubicin bioconjugate.

Formulations based on ONCOFID-S and ONCOFID-D containing certain concentrations of the above bioconjugates have in fact given surprising and completely unexpected results in the treatment of colon-rectal tumours and melanomas both in vitro and in vivo, with a completely different action mechanism from the non-conjugated drug, thus allowing a different use of the bioconjugate as it is particularly effective at dosages different from those currently considered therapeutically active.

The evaluation of the effects on cellular proliferation indicated in Example 10 has surprisingly revealed how ONCOFID® causes a blockage mechanism of cellular proliferation attributable to a differentiative effect of the neoplastic cell which therefore undergoes a reversion process of the phenotype of the malignant neoplastic cell towards an untransformed phenotype, i.e. non-tumoral, by means of:

1. activation of the APC/GSK-3β protein complex for
2. reduction of nuclear accumulation of β-catenin; and for
3. regulation of the processes relating to the action of β-catenin and E-cadherin, thus re-establishing the cellular adhesion capacity and contact inhibition specifically of an untransformed differentiated cell, consequently not inducing the death of the tumoral cell by apoptosis (as is known, on the contrary, for SN38). At the end of their cellular cycle, the above cells die without having produced new metastases and without having contributed to the growth of the primary tumor.

Furthermore, in subsequent experimentations, the Applicant shows how the ONCOFID conjugates are capable of radically modifying the different life phases of the neoplastic cell by causing the drastic drop of phase 1 (defined as gap 1) and phase S, increasing phase 2 (defined as gap 2) in which the cell "remains blocked". This result proves how the ONCOFID conjugates are capable of modulating all the life phases of neoplastic cells (wherein the S phase of DNA synthesis of the cell cycle is highly increased), bringing them to differentiation and blocking the synthesis phases of new DNA, therefore of active cellular proliferation. A blockage of the growing process of the primary tumor and of the metastatization process is consequently obtained.

At the end of the experimental tests, Example 13 clearly shows the greatest anti-tumoral efficacy in vivo of the ONCOFID-S conjugates with respect to the non-conjugated drug with the same dose administered.

As shown in the results, the use of the drug in question as a new pharmacological therapy for neoplasias, is possible as the HA-SN38 conjugate causes a considerable reduction in the systemic toxicity of SN38 thus increasing the therapeutic index of the drug itself, as it is soluble in water and more effective at much lower dosages than those normally used in clinical protocols.

The present invention discloses and claims the use of bioconjugates consisting of hyaluronic acid bound to antitumoral drugs:

for the preparation of a differentiating agent of neoplastic cell towards a untransformed non-tumoral phenotype for the treatment of neoplastic pathologies;

for the preparation of a medicament for treating neoplastic pathologies associated with the nuclear accumulation of β-catenin;

for the preparation of a medicament for treating neoplastic pathologies associated with the inactivation of the APC-GSK-3β complex;

for the preparation of a medicament for treating neoplastic pathologies associated with the increase of the S phase of tumoral cell life;

for the preparation of a medicament for treating the primary tumor or its metastasis.

Examples of such neoplastic pathologies associated respectively to the nuclear accumulation of β-catenin, the inactivation of the APC-GSK-3β complex and the increase of the S phase of tumoral cell life are: breast, skin (and in particular melanoma), bones, brain, thyroid and head and neck tumours, tumours of the lymphatic system, lungs and in the mesothelium, oesophagus, stomach, colon, colon-rectum, pancreas, liver, kidneys, ureters and bladder, prostate, endometrium and ovaries (with all the other abdominal organs) cancer.

The above drug can be administered systemically, (endogenous or arterial, intramuscular, intraperitoneal, intralymphatic, subcutaneous or oral application), intrathecally, it can be used for a topic application (with a transdermal absorption or by endrotracheal instillation), or it can be administered directly in the tumoral site by direct injection (loco-regional treatment).

In the following examples, the Applicant has shown how the preparation of HA conjugates with antitumoral drugs such as SN38 (ONCOFID-S) and Doxorubicin (ONCOFID-D), with a derivatization degree of 1 to 20% weight/weight, produces ONCOFID derivatives which are soluble and effective in aqueous solutions at a concentration of 2 to 15 mg/ml.

In particular, the Applicant has demonstrated, by means of experimental studies in vitro effected using tumoral cellular lines of adenocarcinoma of the colon and human melanoma (necessary for understanding the action mechanism), a completely unexpected biological and pharmacological behaviour of the above bioconjugates. From these data, it can be deduced that the blockage of the cellular proliferation occurs with a mechanism different from the apoptotic action of the reference drug, thus making the derivative of ONCOFID® a drug with a new therapeutic activity and a much higher efficacy obtained with different dosages, for the treatment of neoplasias such as tumours of the breast, skin (and in particular melanoma), bones, brain, thyroid and head and neck tumours, tumours of the lymphatic system, lungs and in the mesothelium, oesophagus, stomach, colon, colon-rectum, pancreas, liver, kidneys, ureters and bladder, prostate, endometrium and ovaries (with all the other abdominal organs). To demonstrate this, the Applicant provides the results of ex-vivo studies obtained from explanted tissues after administration in vivo of the conjugates, and the results of studies in vivo which have revealed the surprising tumoral inhibition capacity of ONCOFID®.

ONCOFID® (as previously described) identifies a new group of bioconjugates based on Hyaluronic Acid (HA) and antitumoral drugs covalently bound through a spacer, which comprise:

antimetabolites such as for example, analogues of folic acid (among which methotrexate), analogues of pyrimidine (among which 5-fluorouracyl and 1-β-D-Arabinofuranosyl-cytosine, (Ara-C));

alkaloids/natural products, such as for example, vincristine and vinblastine (alkaloids of Vinca), the active metabolite of irinotecan: SN38, Taxanes such as paclitaxel and docetaxel;

antibiotics and analogous products, such as for example, doxorubicin and epirubicin;

biological response modifiers;

diterpenoids;

alkylating agents, for example, nitrosoureas;

coordination complexes of platinum, such as for example carboplatinum and cisplatinum;

synthetic hormones and antihormones, such as, for example, estradiol.

Particularly suitable for the purposes of the present invention are doxorubicin, paclitaxel and the metabolite of irinotecan, SN38.

The hyaluronic acid used in the present invention has a molecular weight varying from 400 to 3,000,000 Da, preferably from 5,000 to 1,000,000 Da, and even more preferably from 30,000 to 500,000 Da; it can be of an extractive, fermentative or biosynthetic origin. The covalent bond with the spacer involves the carboxylic group of the D-glucuronic acid of the repetitive unit of the polymer, in a percentage ranging from 1 to 100% (substitution degree), which forms an ester or amide bond with the functional group of the molecular spacer selected which therefore acts as a connection between the hyaluronic acid and chemotherapeutic drug. The spacer agent consists of an aliphatic, araliphatic, alicyclic or heterocyclic chain, linear or branched, with or without heteroatoms, which comprises hydroxyl, carboxyl, carbonyl, amine groups (excluding hydrazides and polypeptides), epoxy groups, acid chlorides, thiols, nitriles, halogens, anhydrides, isocyanates, and isothiocyanates; bromides, iodides and chlorides of carboxylic acids with a $C_2$-$C_{10}$ aliphatic chain, are preferred, and in particular bromides such as bromo propionic acid, bromo butyric acid, bromo butanol or bromo propanol. The substitution degree preferably ranges from 1 to 50% weight/weight, and even more preferably from 1 to 25%; for conjugation with doxorubicin, a substitution of 3 to 20% is preferable whereas for SN38 from 1 to 15% weight/weight.

In particular, ONCOFID-P is the conjugate between HA and Paclitaxel, ONCOFID-S is the conjugate between HA and SN38, ONCOFID-D is the conjugate between HA and Doxorubicin and ONCOFID-Pt is the conjugate between HA and cisplatinum.

More specifically, ONCOFID-S is the ester derivative of HA (having a molecular weight of 200 kDa) and SN38 previously linked to a spacer with four carbon atoms such as bromo butyric acid. The substitution degree can vary from 1 to 15% on the basis of the molar ratio used during the synthesis phases.

The synthesis of ONCOFID-S is widely described in the detailed description and in examples 1-2 of patent application PCT Publ. N. WO2007/014784.

ONCOFID-D is an ester of hyaluronic acid with a spacer such as bromo butanol or bromo propanol, in turn bound to doxorubicin by means of a carbamic bond.

The synthesis of ONCOFID-D is also widely described in the detailed description and in Example 10 of patent application PCT Publ. N. WO2007/014784.

ONCOFID-P has been previously widely described in patent application PCT Publ. N. WO2004/035629.

Finally, the Applicant describes the preparation of different aqueous pharmaceutical formulations in which the bioconjugates in question have proved to be particularly soluble (i.e. in presence of β-cyclodextrin, glucose or liposomes), but above all formulations which allow the administration of the active principles at therapeutically active doses without problems linked to the bioavailability/solubility of the drugs in question, thus contributing with the new chemical/physical/therapeutic properties described above and demonstrated below, to increasing the efficacy.

Some examples of the preparation of ONCOFID formulations are provided hereunder for purely illustrative and non-limiting purposes, together with some examples of in vitro, ex vivo and in vivo studies which show the particular biological behaviour of the conjugates described above.

Example 1

Preparation of an Ester Derivative of Hyaluronic Acid with MW 200 kDa and SN-38 with a Substitution Degree of about 8%

First phase: 500 mg of SN-38 are dissolved in DMF. 0.8866 g of EDC, 0.7011 of 4-Bromobutyric acid and finally 0.1163 g of DMAP are subsequently added.

The reaction is monitored by means of TLC (Silica gel 60 $F_{254}$), using a mixture of $CHCl_3/CH_3CN$ 60/40.

After about 1 h the reaction is considered concluded and 10 ml of methanol are added and the mixture is stirred for about 30'. The product is then precipitated in water, filtered, added to $CHCl_3$, and washed with $H_2O$, slightly acidified with HCl (pH≈4), by means of a separator funnel.

The dried organic phases give a yellowish product which is purified in a gravity chromatography column and gradient eluted, from $CHCl_3$ 1000 to $CHCl_3/CH_3OH$ 95:5.

The BrC4SN38 recovered is dried in a rotavapor and left to dry for a night.

Second phase: 1.4347 g of HATBA (200 kDa) (tetra-alkyl ammonium or tetrabutyl ammonium salt of hyaluronic acid) are charged into a 3 necks glass jacketed reactor and magnetic stirring, and are dissolved in 100 ml of DMSO; the mixture is stirred until complete dissolution, the reactor being thermostat-regulated at 38° C.

380 mg of the intermediate BrC4SN38 dissolved in DMSO are added to the solution of HATBA and the mixture is left under stirring for about 48 hrs at 38° C.

At the end of the reaction, 14 ml of a saturated solution of NaBr are added and the mixture is stirred for about 60 minutes to complete the exchange of TBA-Na cations and obtain sodium HA. Precipitation is then effected with ethanol; the solid obtained is recovered by filtration on Gooch 4 and transferred to a beaker for subsequent washings with Ethanol and is finally dried under vacuum at 40° C.

Example 2

Preparation of an Ester Derivative of Hyaluronic Acid with MW 200 kDa and SN-38 with a Substitution Degree of about 3.5%

First phase: 199 mg of SN-38 are dissolved in 100 ml of ACN and 383 mg of 1-(3-dimethylaminopropyl)-3-ethylcarbodiimide (EDC), 258 mg of 4-bromobutyric acid and 60 mg of DMAP are added to the solution. The trend of the solution is monitored by means of TLC chromatography (silica stationary phase with fluorescence indicator and chloroform-acetonitrile eluent 60:40). The product is recovered by the elimination of the solvent at a rotavapor and purified by chromatography on a silica column. The intermediate thus obtained is dried at room temperature under a high vacuum and finally weighed.

Second phase: 160 mg of BrC4SN38 intermediate are dissolved in 20 ml of NMP and subsequently added to a solution of HATBA 1.2 g in 120 ml of NMP previously thermostat-regulated at 38° C. The mixture is left at 38° C. for 72 h and then diluted with 5 ml of water and 8 ml of a saturated solution of sodium bromide. The whole mixture is left under stirring for 1 hour to allow the exchange of the sodium with the TBA ion. The product is then precipitated by the addition of ethanol dropwise and finally purified by washings in ethanol and dried under vacuum at 40° C.

Example 3

Preparation of an Ester Derivative of Hyaluronic Acid with MW 200 kDa and Doxorubicin with a Substitution Degree of about 10%

First phase: 770 mg of hydrochloric Doxorubicin are weighed and dissolved in 120 ml of anhydrous DMF in the presence of 770 µl of triethylamine, 560 mg of 3-bromo butanol, previously activated with N-hydroxysuccinimide, are subsequently added. The reaction is monitored by means of TLC chromatography (silica stationary phase with fluorescence indicator and chloroform-ethanol eluent 80:20) and is considered concluded after 15 minutes. The product is precipitated in demineralized water and is recovered by filtration on Gooch 5. The solid residue, added to $CHCl_3$, is washed with $H_2O$, slightly acidified with HCl (pH≈4), by means of a separator funnel.

The dried organic phases give a dark red product which is charged into a gravity chromatography column and gradient eluted, from $CHCl_3$ 100% to $CHCl_3/CH_3CH_2OH$ 95:5, for purification.

The intermediate BrC3ODox recovered is dried in a rotavapor and left to dry for a night.

Second phase: 964 mg of HATBA (200 kDa) are charged into a 3 necks glass jacketed reactor and magnetic stirring, and are dissolved in 100 ml of DMSO; the mixture is stirred until complete dissolution, the reactor being thermostat-regulated at 38° C.

550.5 mg of intermediate BrC3ODoxo sciolti in DMSO are added to the solution of HATBA; the reaction is maintained under stirring for about 48 hours at 38° C.

At the end of the reaction, 8 ml of a saturated solution of NaBr are added dropwise and the mixture is stirred for about 30 minutes to complete the exchange of TBA-Na cations and obtain sodium HA. Precipitation is then effected with ethanol; the solid obtained is recovered by filtration on Gooch 4 and transferred to a beaker for subsequent washings with ethanol and is finally dried under vacuum at 40° C.

Example 4

Preparation of an Ester Derivative of Hyaluronic Acid with MW 200 kDa and a Platinized Compound with a Substitution Degree of about 12%

Figure 3:
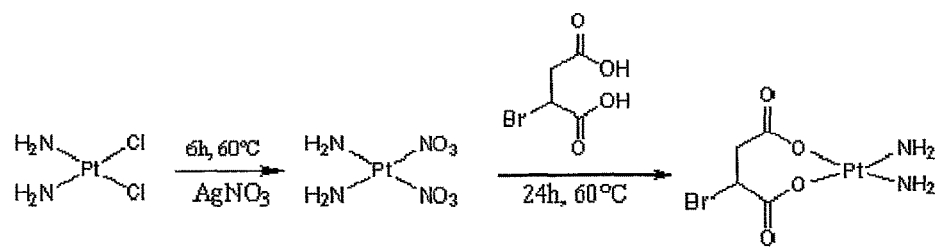
FIG. 3 depicts a synthesis scheme of the intermediate Bromosuccinatediamino-platinum.

200 mg of cis-diamino(dichloro) platinum (II) (0.666 mmol) are dissolved in 20 ml of demineralized water and reacted for 6 h at 60° C. with two equivalents of $AgNO_3$ to be converted into diamine(dinitrate) platinum (II). 140 mg of bromosuccinic acid (0.7 mmol) are then added and the exchange reaction of the ligands is carried out at 60° C. for 24 h. FIG. 3 shows a synthesis scheme of the intermediate Bromosuccinatediamino-platinum. The synthesis intermediate is precipitated and purified for the subsequent reaction with hyaluronic acid.

240 mg of Bromosuccinatediamino-platinum (II) are dissolved in 20 ml of DMSO and slowly added to a solution of hyaluronic acid tetrabutyl ammonium salt (HATBA) in DMSO (1.750 g in 150 ml). The reaction is carried out at 38° C. for 48 h, after which 14 ml of a saturated solution of NaBr are added, under stirring for about 60 minutes in order to complete the exchange of TBA-Na cations and obtain sodium HA. Precipitation is then effected with ethanol; the solid obtained is recovered by filtration on Gooch 4 and washed with ethanol and is finally dried under vacuum at 40°

C. The platinum content of the conjugate is determined via the ICP (inductively coupled plasma) technique.

Example 5

Preparation of a Solution Based on Oncofid-Pt in a Glucosate Solution at 5% w/v 60 mg of ONCOFID-Pt, obtained as described in Example 4, with a substitution degree on the carboxylic residues of 3 to 156 w/w, are dissolved in 29 ml of aqueous solution containing 5% w/v of glucose. The solution is left under magnetic stirring until the complete dissolution of the conjugate; it is then filtered on sterilizing filters on regenerated cellulose (RC) with a 0.22 µm syringe. The titer of the solution (3 mg/ml in ONCOFID) is determined by means of spectrophotometry before and after filtration to verify a total recovery of the conjugate after filtration.

Example 6

Pharmaceutical Preparation Based on ONCOFID-S in a Solution of β-cyclodextrin at 1.5% w/v 62 mg of ONCOFID-S, obtained as previously described, with a substitution degree on the carboxylic residues of 3 to 15 w/w, are dissolved in 22 ml of aqueous solution containing 1.5% w/v of β-cyclodextrin. The solution is left under stirring with a magnetic stirrer until the complete dissolution of the conjugate; it is then filtered on sterilizing filters on regenerated cellulose (RC) with a 0.22 µm syringe. The titer of the solution (2.8 mg/ml in ONCOFID-S) is determined by means of spectrophotometry before and after filtration to verify a total recovery of the conjugate after filtration.

Example 7

Pharmaceutical Preparation Based on Oncofid-S in a Solution of Glucose at 5% w/v 56 mg of ONCOFID-S, obtained as previously described, with a substitution degree on the carboxylic residues of 3 to 15% w/w, are dissolved in 20 ml of aqueous solution containing 5% w/v of glucose. The solution is left under stirring with a magnetic stirrer until the complete dissolution of the conjugate; it is then filtered on sterilizing filters on regenerated cellulose (RC) with a 0.22 µm syringe. The titer of the solution (2.8 mg/ml in ONCOFID-S) is determined by means of spectrophotometry before and after filtration to verify a total recovery of the conjugate after filtration.

Example 8

Pharmaceutical Preparation Based on ONCOFID-P in a Solution of Glucose at 5% w/v 100 mg of ONCOFID-P, obtained as described in Examples 5, 6, 7, 9 and 10 of the patent WO2004035629, are dissolved in 20 ml of aqueous solution containing 5% w/v of glucose. The solution is left under stirring with a magnetic stirrer until the complete dissolution of the conjugate; it is then filtered on sterilizing filters on regenerated cellulose (RC) with a 0.22 µm syringe. The titer of the solution (5 mg/ml in ONCOFID-P) is determined by means of spectrophotometry before and after filtration to verify a total recovery of the conjugate after filtration.

Example 9

Pharmaceutical Preparation Based on ONCOFID-D in a Glucosate Solution at 5% w/v 60 mg of ONCOFID-D, obtained as previously described, with a substitution degree on the carboxylic residues of 3 to 15% w/w, are dissolved in 20 ml of aqueous solution containing 5% w/v of glucose. The solution is left under stirring with a magnetic stirrer until the complete dissolution of the conjugate; it is then filtered on sterilizing filters on regenerated cellulose (RC) with a 0.22 µm syringe. The titer of the solution (3 mg/ml in ONCOFID-D) is determined by means of spectrophotometry before and after filtration to verify a total recovery of the conjugate after filtration.

Example 10

In Vitro Experimentation of the Bioconjugate ONCOFID-S in Preclinical Models of Adenocarcinoma of the Colon The objective of this experimentation in vitro is mainly to define the activity profile of the bioconjugate consisting of HA bound to the SN38 prepared in Example 2 formulated in aqueous solution, to evaluate/compare the antineoplastic activity of ONCOFID derivatives vs the reference drugs, thus determining their pharmacological capacity relating to the comparative antineoplastic agent and action mechanism.

Products Tested and Active Principles Tested
  SN38: control reference product;
  ONCOFID-S: ester derivative of HA covalently bound to SN38 with an esterification % at the carboxyl (w/w) of 3.5%

Pharmaceutical Preparations Tested
  The SN28 was dissolved in a mixture consisting of DMSO/CH$_3$CN/EtOH (10:45:45) at room temperature.
  Solution of ONCOFID-S in β-cyclodextrin: prepared as described in the Example 6.

Cellular Lines Used
  Adenocarcinoma cells of the colon of a rat DHD/K12/Trb expressing the receptor for HA CD44

Experimental Protocol
  1) the cellular line being examined is plated at a concentration of 6×10$^4$ cells per cm$^2$, in plates with 24 wells with a flat bottom;
  2) after 24 hours, the solutions to be tested, suitably diluted in the culture medium, are added to the cells;
  3) 24 or 48 h after treatment, the cell vitality is evaluated with the Tripan blue exclusion method, a dye extruded from vital and metabolically active cells, withheld however by the dead cells which become blue-coloured.

Results

The results obtained in terms of the vitality of the cells DHD/K12/Trb in relation to the dose, in addition to the IC50 values of the new conjugate ONCOFID-S compared with that of non-conjugated SN38 after 24 h of treatment, showed a greater efficacy of ONCOFID-S with respect to SN38. The IC50 values of SN38 as such and ONCOFID-S were found to be 1.4 µg/ml and 0.4 µg/ml respectively. Considering that the conjugate ONCOFID-S in question was derivatized at 3.5% by weight in SN38, the IC50 value of the SN38 equivalent (conjugated to HA) is even lower (0.014 µg/ml) i.e. 100 times more active than the reference drug, confirming a potentiation of its pharmacological efficacy when it is conjugated with hyaluronic acid.

Figure 4:
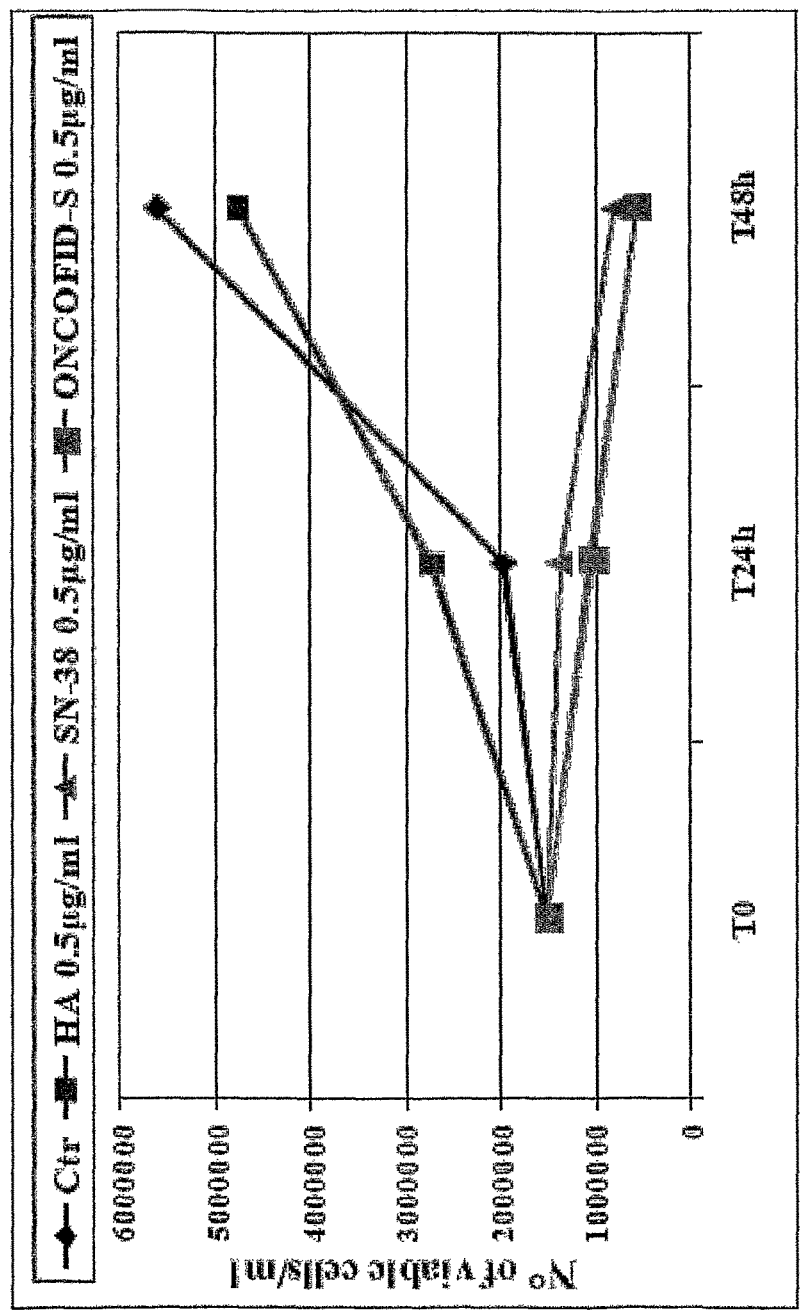
FIG. 4 depicts the cellular vitality graph in relation to the time after treatment with HA, SN38 or ONCOFID-S at a concentration of 0.5 µg/ml.

FIG. 4 shows the cellular vitality graph in relation to the time after treatment with HA, SN38 or ONCOFID-S at a concentration of 0.5 µg/ml.

Due to the importance of the role of regulating the β-catenin in the formation and progression of colon-rectal carcinomas, it was verified whether the treatment with Oncofid-S is capable of modifying the intracellular expression and distribution of the molecules involved in the control process of the above protein, as previously described. The effect of the treatment with ONCOFID-S on the intracellular distribution of E-cadherin, β-catenin, APC e GSK-3β in the DHD/Trb cells was therefore analyzed by means of fluorescence microscopy. Specific antibodies were used for the above proteins, visualizing them with the use of secondary antibodies bound to fluorochromes such as rodamin and fluoroescein.

Figure 4A:
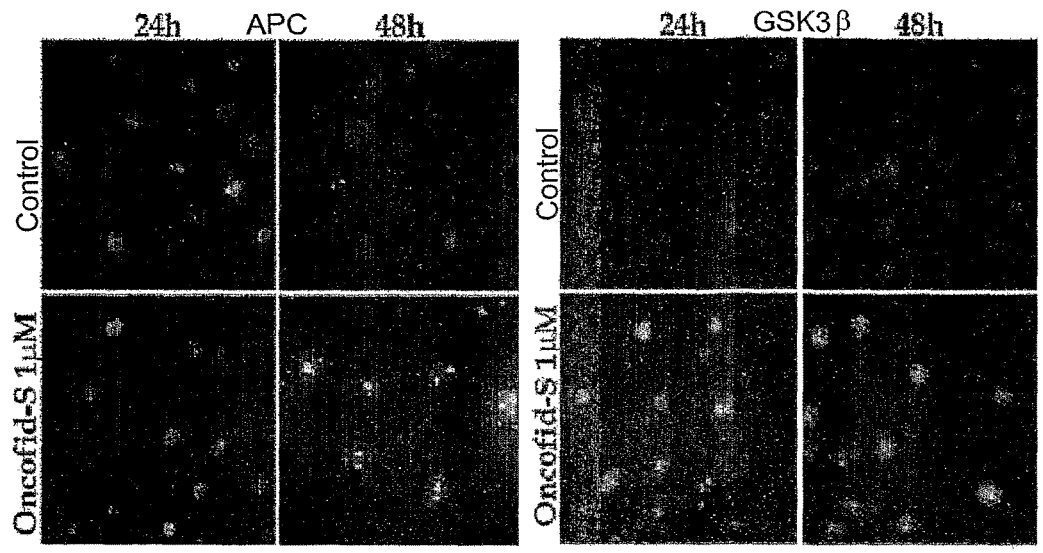
FIG. 4a depicts the translocation into the nucleus of both the APC protein and GSK-3β kinase.
Figure 4B:
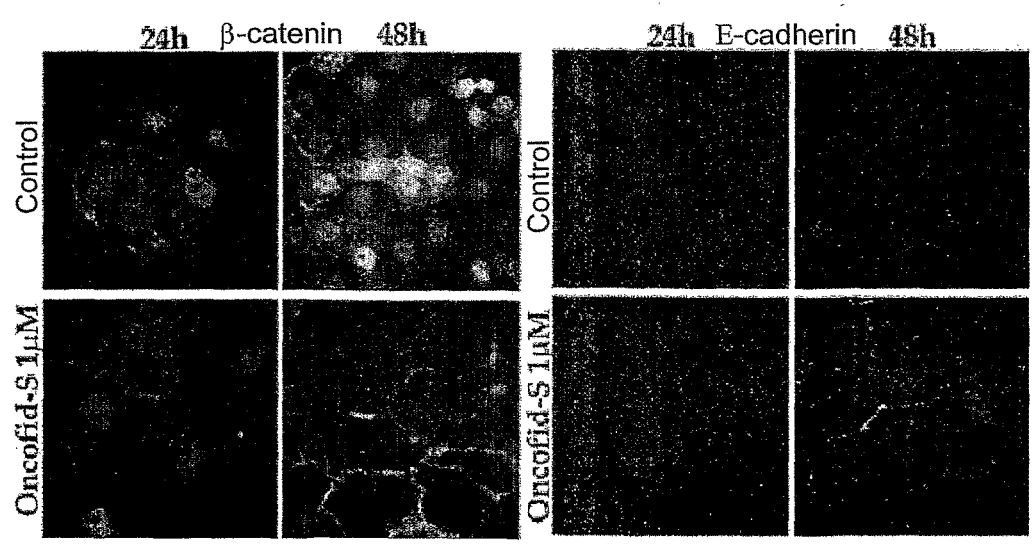
FIG. 4b depicts the translocation of β-catenin from the nucleus to the cytoplasm.
Figure 5:
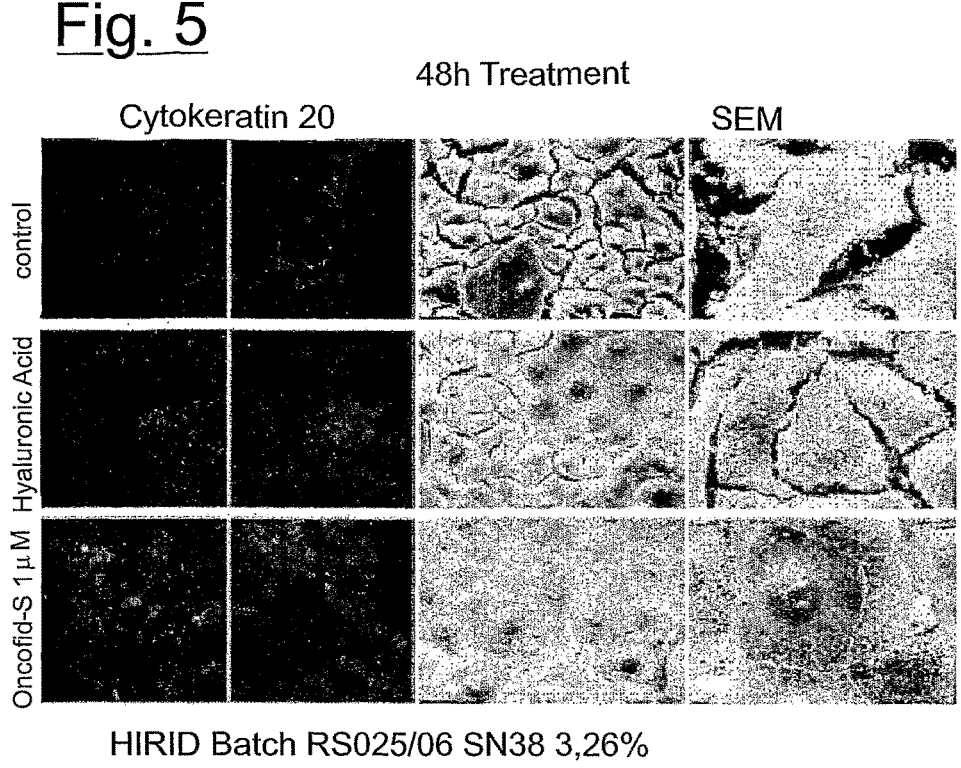
FIG. 5 depicts the scanning electron microscope analysis (SEM) of the morphological modifications induced by the in vitro treatment on the tumoral cells analyzed after experimentation.

The results obtained showed that the anti-proliferative and therefore antitumoral effect, of the treatment with the bioconjugate Oncofid-S shown in FIG. 4, is preceded by:
- the translocation into the nucleus of both the APC protein and GSK-3β kinase (FIG. 4a), where they are able to regulate the accumulation of β-catenin by means of phosphorylation (as previously indicated) with a consequent stoppage in the cell proliferation;
- the translocation of β-catenin from the nucleus (wherein, as previously described, it is known to accumulate and activate oncogenes involved in the proliferation of tumoral cells) to the cytoplasm (FIG. 4b) where, by combining on the level of the cell membrane with E-cadherin, it reforms the E-cadherin-β-catenin intracellular complex which regulates cellular adhesion and represents a clear sign of cell differentiation;
- the consequent increased expression of E-cadherin (FIG. 4b), membrane protein involved in inter-cellular adhesion processes and in the formation of cell-cell joining (which, as is known, have a fundamental role in determining contact inhibition and cell differentiation); the increase in the expression of E-cadherin is, in fact, considered a marker of the differentiation of non-tumoral epithelial cells of healthy colic mucous;
- an increase in the expression of cytokeratin 20 (CK20), $2^{nd}$ marker of the differentiation of non-tumoral epithelial cells of healthy colic mucous (FIG. 5). All of the above modifications relating to cell differentiation are not revealed in the samples treated with non-conjugated SN38.

These data clearly demonstrate that the stoppage mechanism of the proliferation of neoplastic cells in the samples treated with ONCOFID-S shown with FIG. 4, can be attributed to a differentiating effect and not to the induction of a massive cell death by apoptosis, as is known, on the contrary, for SN38.

FIG. 5 shows the scanning electron microscope analysis (SEM) of the morphological modifications induced by the in vitro treatment on the tumoral cells analyzed after experimentation, modifications which confirm the differentiating effect of the bioconjugate with respect to neoplastic cells towards an untransformed phenotype i.e. not tumoral, therefore restoring the inter-cellular adhesion capacity responsible for contact inhibition, thus causing blockage of the proliferation of the tumour.

FIG. 5 shows the effect of ONCOFID-S after 48 h of treatment on CK20 expression and on morphology of the rat colon adenocarcinoma cells DHD/K12/Trb: after treatment the cell number expressing CK20 was increased in comparison to non-treated control and to the cell cultures treated with hyaluronic acid. Cell morphology of cells treated with the bioconjugate shows typical features of the differentiated epithelial cell, such as greater substrate adhesion, greater flattening and presence of tight cell-to-cell junctions.

Conclusions

On the cellular line of adenocarcinoma of the colon, that is positive for the expression of the CD44 receptors, the ONCOFID-S derivative at low doses shows a surprising anti-proliferative effect due not so much to the induction of apoptosis, as observed and known for SN38, as to a differentiation/reversion of the adenocarcinoma cells in untransformed epithelial cells, i.e. non-tumoral, therefore not proliferant. Once they have concluded their cell cycle, the above cells die without creating new metastases and without contributing to the growth of the neoplasia.

Example 11

In Vitro Experimentation of the Bioconjugate Oncofid-S in Preclinical Models of Adenocarcinoma of the Colon The objective of this experimentation in vitro is mainly to define the activity profile of the ONCOFID derivative with a higher derivatization degree and formulated in aqueous glucosate solution, to evaluate/compare the anti-neoplastic activity with that of the reference drug, thus determining the pharmacological capacity relating to the comparative anti-neoplastic agent.

Experimental Scheme

Products Tested and Active Principles Tested:
  SN38: control reference product;
  ONCOFID-S: ester derivative of HA covalently bound to SN38 with an esterification % at the carboxyl (w/w) of 8% prepared according to Example 1.

Pharmaceutical Preparations Tested
  The SN28 was dissolved in a mixture consisting of DMSO/CH$_3$CN/EtOH (10:45:45) at room temperature.
  Solution of ONCOFID-S in glucosate prepared as described in Example 7.

Cellular Lines Used
  Adenocarcinoma cells of the colon of a rat DHD/K12/Trb.

Experimental Protocol
  1) the cellular line being examined is plated at a concentration of 6×10$^4$ cells per cm$^2$, in plates with 24 wells with a flat bottom
  2) after 24 hours, the solutions to be tested suitably diluted in the culture medium are added to the cells
  3) 24 or 48 h after treatment, the cell vitality is evaluated with the Tripan blue exclusion method, a dye extruded from vital and metabolically active cells, withheld by the dead cells which become blue-coloured.

Results

Figure 6:
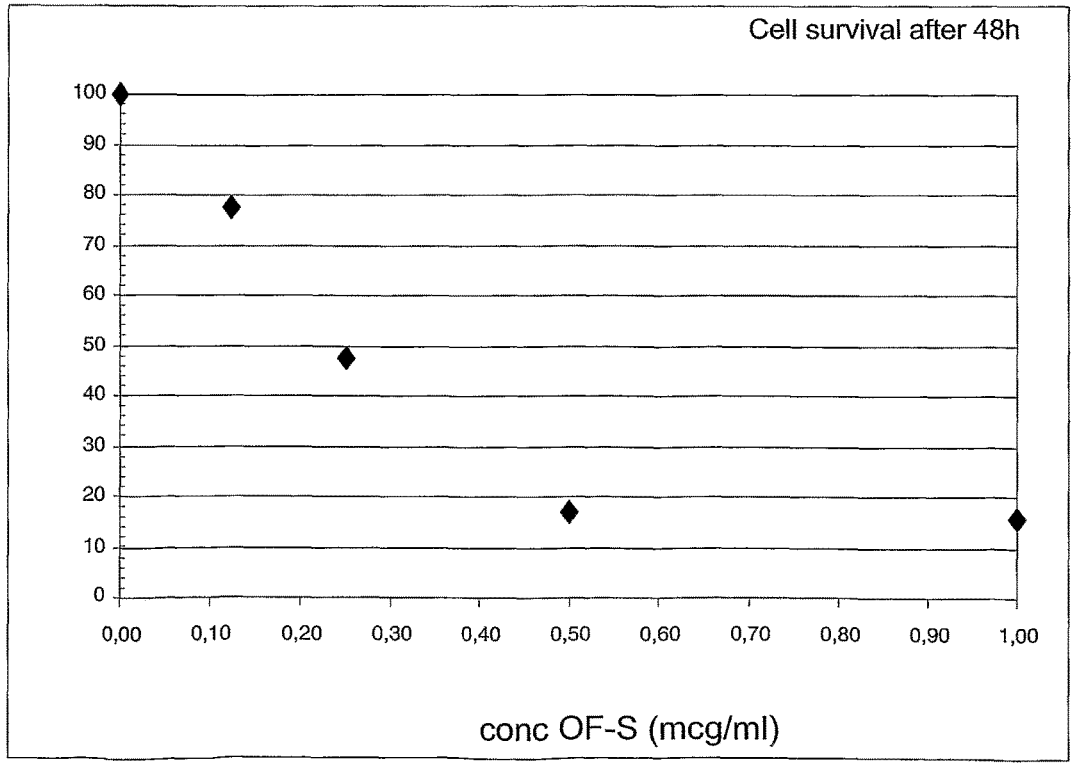
FIG. 6 depicts a graph showing the results obtained in terms of cell vitality in relation to the dose of ONCOFID-S tested after 48h of treatment.

The results obtained in terms of cell vitality in relation to the dose of ONCOFID-S tested (concentrations of 0.125, 0.25 e 0.5 e 1 µg/ml) after 48 h of treatment, are indicated hereunder in graphic form (FIG. 6).

The dose 250 ng/ml corresponds to IC50 and confirms the much higher efficacy of ONCOFID-S prepared according to Example 2, with respect to that prepared according to Example 1 (IC50 equal to 0.4 µg/ml, as indicated in the results of Example 5); consequently the efficacy is much higher than the non-conjugated SN38.

This result can be attributed to the higher derivatization percentage in SN38, i.e. 8% by weight, with respect to the ONCOFID-S (OF-S) derivatized at 3.5%.

A table is provided hereunder, of the IC50 of the 2 conjugates with different substitution degrees (3.5 and 8%) and the respective equivalents in conjugated SN38, with respect to the non-conjugated reference drug SN38.

|  | IC50 |
| --- | --- |
| SN38 non conjugated | 1.4 µg/ml |
| OF-S 3.5% w/w | 0.4 µg/ml |
| SN38 equiv | 0.014 µg/ml |

|  | IC50 |
| --- | --- |
| OF-S 8% w/w | 0.25 µg/ml |
| SN38 equiv | 0.02 µg/ml |

Conclusions

The ONCOFID-S derivative shows an efficacy five times higher than that observed for the non-conjugated SN38 drug but, considering the concentration of equivalent SN38, the efficacy proves to be about 70 times higher than that of the reference drug. Furthermore, a comparison with the studies of the conjugate with a smaller derivatization percentage shows that the more the hyaluronic acid is derivatized in SN38, the greater the efficacy of ONCOFID-S will be.

Example 12

In Vitro Experimentation of the Bioconjugate Oncofid-S in Preclinical Models of Adenocarcinoma of the Colon The objective of the above experimentation is to study the influence of the ONCOFID-S derivative on the various cell life phases to evaluate itS activity vs that of the reference drug SN38.

Experimental Scheme

Products Tested and Active Principles Tested
SN38: control reference product;
ONCOFID-S: ester derivative of HA covalently bound to SN38 with an esterification % at the carboxyl (w/w) of 3.5% prepared according to Example 2;

Pharmaceutical Preparations Tested
The SN28 was dissolved in a mixture consisting of DMSO/CH$_3$CN/EtOH (10:45:45) at room temperature.
Solution of ONCOFID-S in glucosate prepared as described in Example 7

Cellular Lines Used
Adenocarcinoma cells of the colon of a rat DHD/K12/Trb

Experimental Protocol
As described for examples 8 and 9.

Results

The effect of the ONCOFID-S conjugate (at a concentration of 0.5 µg/ml) was determined using an analysis of the cytofluorometric type; after 24 h of pharmacological treatment, the cell phases are identified with FACS-Scan (Becton Dickinson) by cytofluorometric, analysis of the DNA content after colouring the cells with propidium iodide.

FIG. 7 shows the results obtained: the treatment with the conjugate in question causes the drastic collapse of the gap1 and S phases whereas the gap2 phase increases differentiating ONCOFID from the reference drug which, on the contrary, increases both the first phase and the S phase.

In order to evaluate whether the data obtained persist with time, the Wash out test was effected in which, after 48 h of treatment, the culture medium is substituted with fresh medium without treatment: the cell phases were then defined again at the point defined as TO and, after 24 h of culture, T24.

The results obtained can be seen in FIG. 8: they clearly show that even after 24 hours of pharmacological suspension, the blockage of the gap 1 and S phases persists, indicating how the effect of the drug is therefore irreversible.

Conclusions

In every proliferant mammal cell, the replication of its genome and the division of the cell itself take place within specific cell life phases, identified as gap1, S, gap2. In gap1 the cell encounters all those biochemical modifications which must prepare it for phase S in which new DNA is synthesized: in S, in fact, the exact copy of the genetic material of the cell is generated, which will be divided into two daughter cells through the subsequent mitosis process M. The phase which follows S and precedes M, is defined gap2 and is the mitosis preparation phase. The results obtained show how the bioconjugate ONCOFID is effective in the substantial reduction of the most important life phase of the neoplastic cell: the S phase of active synthesis of novel DNA for the subsequent proliferation and growth of the tumour, which is significantly increased in tumoral cells in comparison to non tumoral cells. Therefore, at low doses, the new drug has proved to be capable of modulating the cell growth phases by blocking the tumoral proliferation in a substantially different way from the reference drug SN38.

Example 13

In Vitro Experimentation of the Bioconjugate Oncofid-D in Preclinical Models of Human Melanoma The objective of this experimentation in vitro is mainly to define the activity profile of the derivative ONCOFID-D formulated in aqueous glucosate solution, to evaluate/compare the anti-neoplastic activity with that of the reference drug, thus determining the pharmacological capacity relating to the comparative anti-neoplastic agent (Doxorubicin).

Experimental Scheme

Products Tested and Active Principles Tested
Doxorubicin: control reference product;
ONCOFID-D: ester derivative of HA covalently bound to Doxorubicin with an esterification % at the carboxyl (w/w) of 10% prepared according to Example 3;

Pharmaceutical Preparations Tested
The Doxorubicin was dissolved in a glucose solution at 5% w/v at room temperature.
Solution of ONCOFID-D in glucosate prepared as described in Example 9.

Cellular Lines Used
Human melanoma cells M14 expressing the receptor for HA CD44.

Experimental Protocol
the cellular line being examined is plated at a concentration of 6×10$^4$ cells per cm$^2$, in plates with 24 wells with a flat bottom;
after 24 hours, the solutions to be tested, suitably diluted in the culture medium, are added to the cells;
24 hours after treatment, the cytotoxicity is evaluated in confocal microscopy by colouring with a "Live Dead" Cell Vitality Assay test (Molecular Probes, Eugene, Oreg.). The observation was effected by means of a LEICA TCS SP5 confocal microscope.

Results

Figure 9:
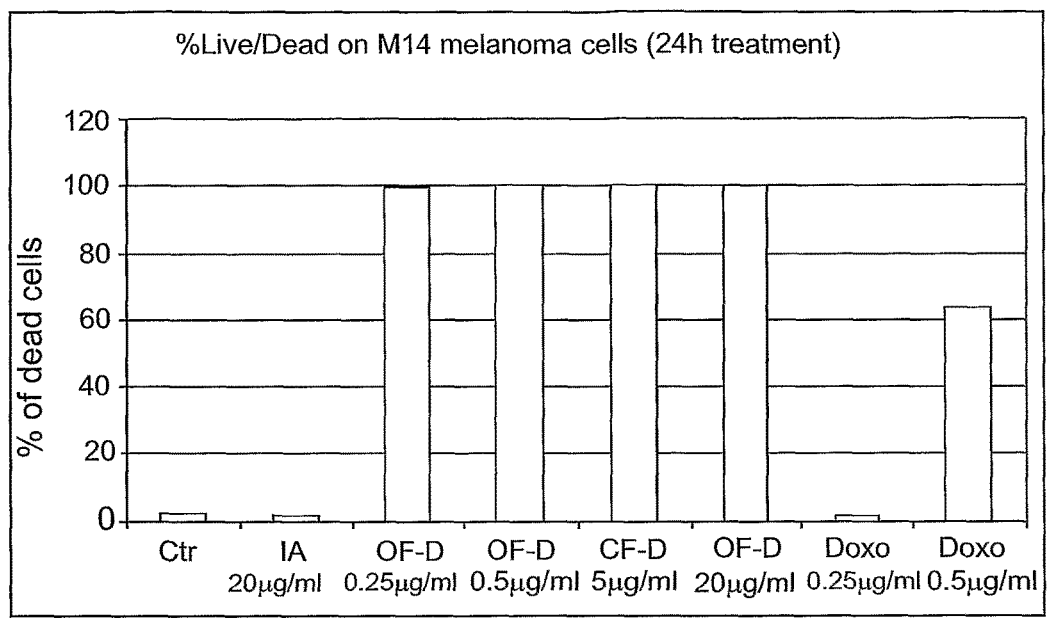
FIG. 9 depicts a graph showing the cytotoxic effect induced by ONCOFID-D (OF-D) and non-conjugated Doxorubicin in relation to the dose after 24h of treatment of the cell line of melanoma M14.

The cytotoxic effect induced by ONCOFID-D (OF-D) and non-conjugated Doxorubicin is indicated hereunder in graphic form (FIG. 9), in relation to the dose (concentrations of 0.25, 0.5, 20 µg/ml) after 24 h of treatment of the cell line of melanoma M14.

Conclusions

The melanoma cell line proved to be strongly positive for the expression of the CD44 receptors; the evaluation of the cytotoxicity in a confocal microscopy indicates that ONCOFID-D is capable of exerting a greater cytotoxic effect on this line of melanoma than the corresponding non-conjugated Doxorubicin. Furthermore, considering that in the bioconjugate ONCOFID-D the percentage of conjugated Doxorubicin is equal to 10% by weight, the activity of the drug is 10 times higher.

Example 14

Evaluation of the Anti-Tumoral Effects In Vivo of the Bioconjugate Oncofid-S in an Experimental Tumour Model Induced in Rats by a Carcinoma Line of the Syngenic Colon In order to confirm the high efficacy shown by ONCOFID derivatives, also by means of in vivo experimentation, in the cytotoxic action in vitro, BDIX rats were used for the induction of abdominal tumours. The inoculation of the cell line DHD/K12/Trb, effected intraperitoneally, in fact, caused the formation of peritoneal carcinomatosis and tumoral ascites.

A comparison was then made of the anti-tumoral capacity in vivo of CPT-11 at a concentration of 40 mg/kg vs ONCOFID-S, again at a concentration of 40 mg/kg (which corresponds to 3.2 mg/kg of the active principle SN38 the bioconjugated being derivatized for 80), both administered intraperitoneally.

The objectives of the study in vivo were the following:
1. evaluating the tumoral growth with respect to the control group and/or the regression or disappearance of the peritoneal tumoral lesions and the observation of ascites;
2. confirm the results of the anti-tumoral effect obtained in the in vitro studies;
3. evaluate the haematological and tissular toxicity caused by the treatment.
Experimental Scheme
Drugs Used: Active Principles Tested
  Irinotecan® (o CPT-11): control reference product;
  ONCOFID-S: ester derivative of HA covalently bound to SN38 with an esterification % at the carboxyl (w/w) of 80 prepared according to Example 1;
Pharmaceutical Preparations Tested
  The Irinotecan was dissolved in a heated (70° C.) glucosate solution at 5% w/v for about 1 hour.
  Solution of ONCOFID-S in glucosate prepared as described in Example 7.
  Animals treated: 36 male rats BDIX 7 weeks' old (about 200 g) were divided according to experimental criteria into the following groups (each group consists of 12 animals):
1. Control Group: inoculum DHD/K12/trb.
2. CPT-11 Group: inoculum DHD/K12/trb+treatment CTP-11 40 mg/Kg intraperitoneally.
3. ONCOFID-S Group: inoculum DHD/K12/trb+treatment ONCOFID-S 40 mg/Kg intraperitoneally.

After 14 days of stabling, $1 \times 10^6$ DHD/K12/trb cells per rat were inoculated intraperitoneally. After 7 days the therapeutic treatment envisaged was initiated, consisting of 4 therapy cycles. The sacrifice of the animals was established 7 days after the last pharmacological treatment. The animals were evaluated once a week for the appearance of possible signs of toxicity, by measuring the body weight, and for the possible appearance of ascites. At the moment of sacrifice an intracardiac sampling was effected in all the animals and the haematological toxicity due to the pharmacological treatment was evaluated. The tumours and ascites were removed and measured. The tissues removed were fixed in formalin for histological and immunohistochemical evaluation.
Results
Evaluation of the volumes of peritoneal carcinomatosis.

Figure 10:
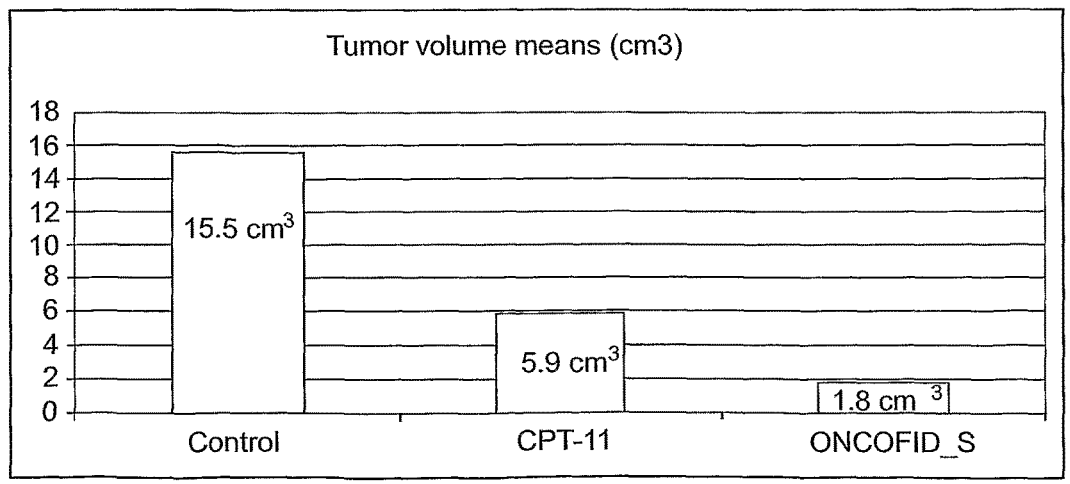
FIG. 10 depicts a graph showing the evaluation of the growth of tumoral modules at the end of the treatments.

The evaluation of the growth of tumoral nodules was effected at the end of the treatments; FIG. 10 shows how at the end of the test (T28), the volume of the average of the tumours revealed a good response to the treatment in the group CPT-11 (5.9 cm$^3$) and an excellent response in the group of ONCOFID-S (1.8 cm$^3$) with respect to the non-treated control group (15.5 cm$^3$).
Evaluation of the Presence of Bloody Ascites Bloody ascites is due to the dissemination of a tumour in the peritoneal cavity; clinically, it is mainly associated with tumours of a gastrointestinal and ovarian origin. The mechanism responsible for the formation of malignant ascites is above all blockage of the lymphatic drainage, it has been demonstrated, however, that when the concentration of the tumoral cells in the ascitic fluid is high (>4.000/mm$^3$), their presence alone can produce ascites due to the production of chemical mediators (cytokines, histamine, lactic acid) with an irritating effect.

Figure 11:
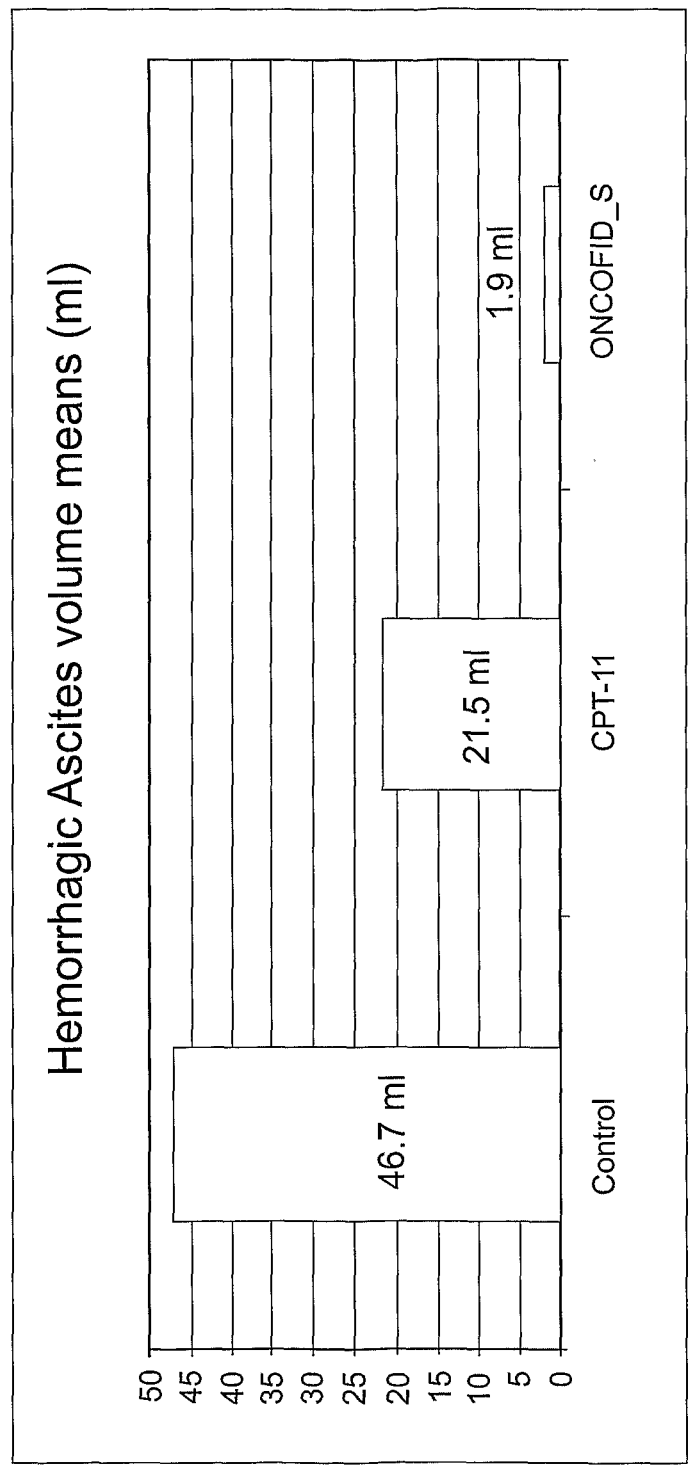
FIG. 11 depicts a graph showing the average volume of bloody ascites at the end of the treatments.

FIG. 11, in perfect coherence with the result of tumoral volumes, shows how at the end of the test (T28) the average volume of bloody ascites (tumoral) taken is 46.7 ml in the control, 21.5 ml in the group treated with CPT-11 and only 1.9 ml in the group treated with ONCOFID-S.

Figure 12:
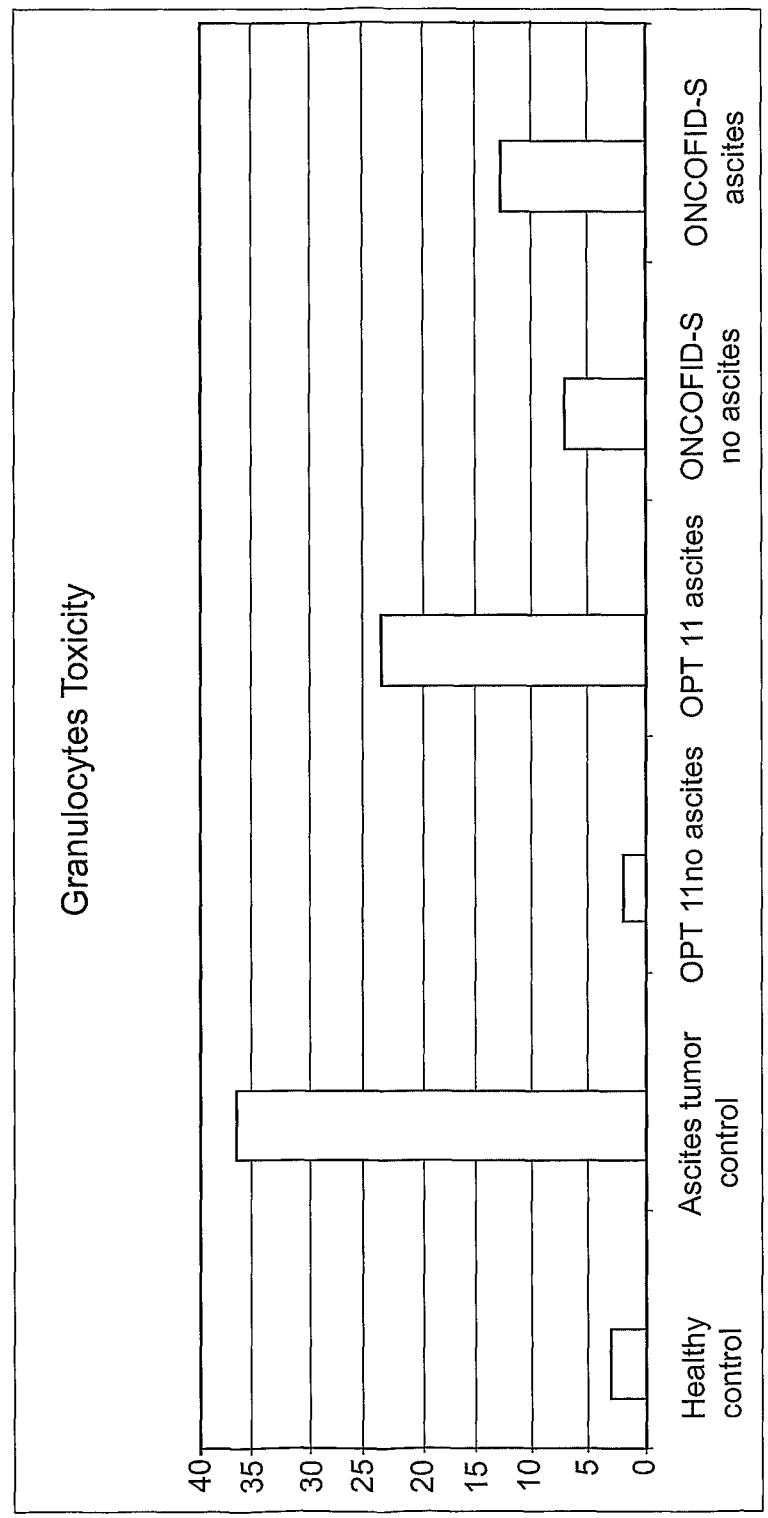
FIG. 12 depicts a graph illustrating the analysis of the haematocytometric profile of the animals treated.

It should be noted that whereas 100% and 83% of the animals of the control group and group treated with CPT-11 had bloody ascites, only 16% of the animals of the group treated with ONCOFID-S had modest quantities of ascites.
Evaluation of the Haematological Toxicity:

FIG. 12 illustrates the analysis (at T 28) of the haematocytometric profile of the animals treated. The values of the granulocytes, population of white globules which are mostly influenced by the chemotherapeutic treatment are indicated.

In the group treated with ONCOFID-S without ascites, no leukopenia from pharmacological toxicity is registered, whereas the animals which have developed a modest ascites have a number of granulocytes which falls within the norm, thus confirming the non-toxicity of the bioconjugate object of the present invention.
Conclusions In line with the results obtained from in vitro studies, the experimentation in vivo shows a surprising difference in efficacy of the drug conjugated to HA with respect to the free drug. Not only does the derivative ONCOFID-S cause an average reduction in the tumoral mass of 88% (vs 62% in the group treated with CPT-11), but from the haematological toxicity data and measurement of the volume of ascites, an index of the progression of the tumor, a reduced pharmacological toxicity induced by the treatment in question is observed.

Example 15

Ex Vivo Studies for Evaluating the Action Mechanism of the Bioconjugate Oncofid-S In order to confirm the surprising biological/pharmacological behaviour of the ONCOFID derivatives, which demonstrated an anti-proliferative effect of the differentiative rather than apoptotic type, the tumours induced as described above were explanted to effect immunohistochemical studies.
Experimental Protocol The tumours explanted immediately after extraction, were carefully washed with a physiological solution, fixed with buffered formalin, processed for inclusion in paraffin and cut into sections having a thickness of 4 μm. The histological analysis was carried out on sections coloured with haematoxylin/eosin whereas the immunological analysis was effected with the use of specific antibodies for the proteins studied, revealed with the help of secondary antibodies bound to peroxidase for an analysis which could be effected with an optical microscope.

Results

From the ex-vivo immunohistochemical analysis of the intraperitoneal tumours, confirmation was provided of the data obtained in vitro on the action mechanism of the bioconjugate relating to the regulation of the E-cadherin-β-catenin complex, for the induction of an effect of the differentiating and therefore non-proliferative rather than apoptotic type.

Figure 13:
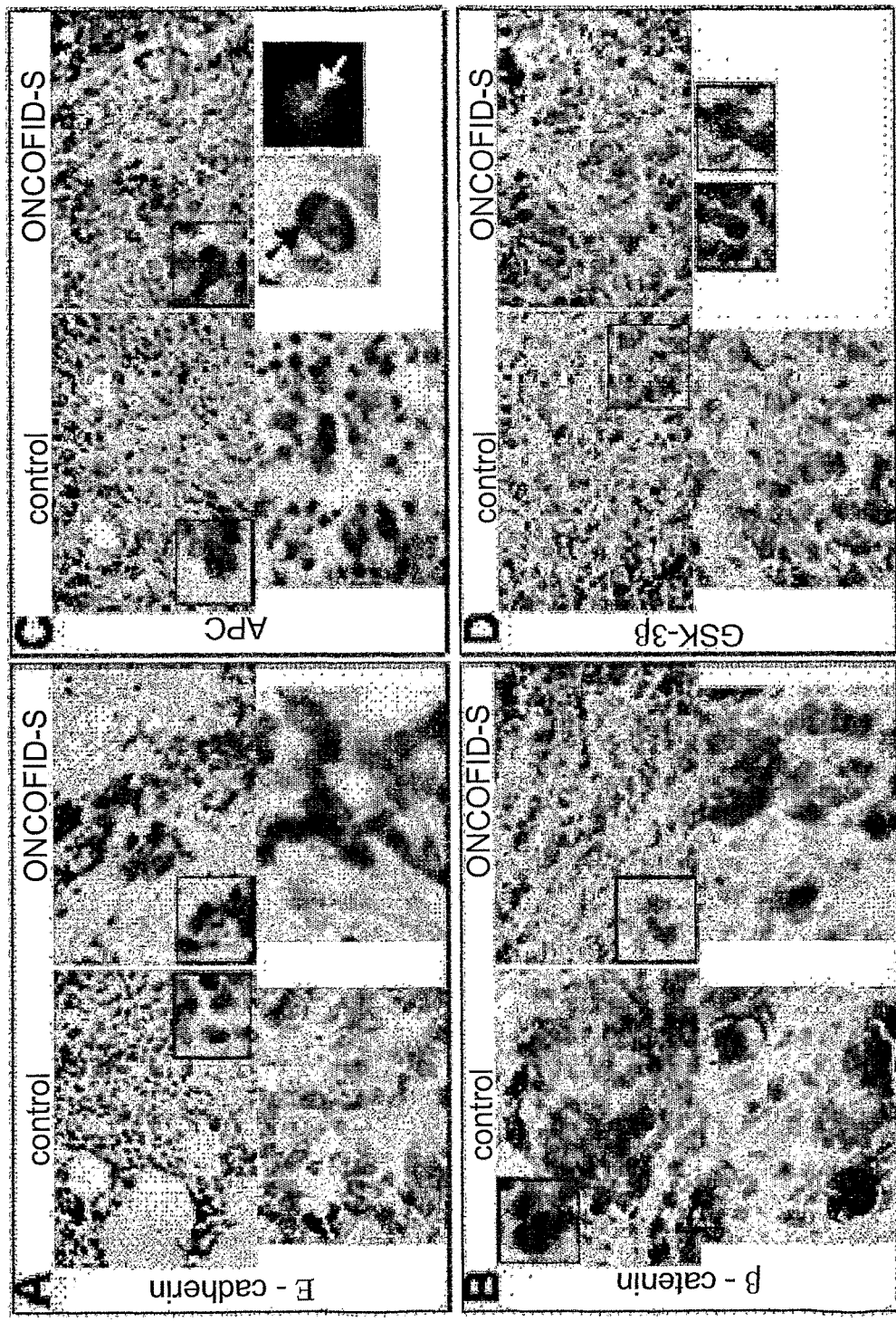
FIG. 13 depicts the reversion of the undifferentiated tumoral phenotype towards a differentiated and no longer proliferant phenotype.

In short, the results obtained from the ex-vivo analysis are the following:
1) in the tumours explanted from animals treated with ONCOFID-S an expression pattern of the oncoprotein/onco-soppressor complexes can be observed which is completely similar to what was observed in the cell model used in vitro, indicating the reversion of the tumoral phenotype towards a normal phenotype. In the tumours explanted from the animals treated with ONCOFID-S, β-catenin, in fact, there is a shift from the nucleus towards the cell-cell junctions whereas the APC protein and GSK3β protein move into the nucleus (FIG. 10).
2) E-cadherin and CK20, markers of the differentiation of the epithelial cells of the colic mucous, in the tumours explanted from the animals treated with ONCOFID-S have an increased expression with respect to the control animals, exactly as observed in the cell model treated in vitro. This increased expression is also indicative of the reversion of the undifferentiated tumoral phenotype towards a differentiated and no longer proliferant phenotype as it is no longer tumoral (FIG. 13).

Conclusions

The particular biological/pharmacological behaviour of the ONCOFID derivative is consequently also confirmed in vivo, in blocking cell proliferation, promoting the differentiation of tumoral cells towards an untransformed non-tumoral phenotype.

In view of the above description of the invention, it is evident that these methods can be variably modified. These modifications should not be considered as divergences from the spirit and perspectives of the invention and all the modifications which can appear evident to an expert in the field are included in the scope of the following claims.

The invention claimed is:

1. A method for differentiating a neoplastic cell towards a non tumoral untransformed phenotype which comprises exposing a neoplastic cell to at least one bioconjugate consisting of hyaluronic acid bound to an antitumoral drug for differentiating a neoplastic cell towards a non-tumoral untransformed phenotype, wherein said method avoid the nuclear accumulation of β-catenin protein and activates the APC-GSK-3β protein complex, and wherein the drug is doxorubicin, covalently bound through a spacer selected from bromobutanol or bromopropanol, with a substitution degree of doxorubicin at carboxyl of hyaluronic acid ranging from 3 to 20%, wherein said hyaluronic acid is bound to said spacer via an ester bond with the carboxyl moiety in said hyaluronic acid and said spacer is bound to said doxorubicin via a carbamic bond.

2. The method according to claim 1, wherein said method treats a tumour of the breast, skin, bones, brain, thyroid and for head-neck tumours, tumours of the lymphatic system, lungs and in the mesothelium, of the esophagus, stomach, colon, pancreas, liver, kidneys, ureters and bladder, prostate, endometrium or ovaries.

3. The method according to claim 1, wherein said method treats a tumour of the colon-rectum.

4. The method according to claim 1, wherein said method treats melanoma.

5. The method according to claim 1, wherein said bioconjugate is administered by systemic administration, topical administration or direct injection into the site of the tumour.

6. The method according to claim 5, wherein said administration is carried out by intravenous, arterial, intramuscular, transdermal, intraperitoneal, intrathecal, intralymphatic application, application by endotracheal instillation, subcutaneous, oral or locoregional application.

7. The method according to claim 1, wherein the hyaluronic acid has a molecular weight ranging from 400 to $3 \times 10^6$ Da.

8. The method according to claim 7, wherein the hyaluronic acid has a molecular weight ranging from 5,000 to $1 \times 10^6$ Da.

9. The method according to claim 8, wherein the hyaluronic acid has a molecular weight ranging from 30,000 to $0.5 \times 10^6$ Da.

10. A pharmaceutical formulation containing at least one bioconjugate consisting of hyaluronic acid bound to an antitumoral drug together with one or more pharmacologically acceptable adjuvant and/or excipient for differentiating a neoplastic cell towards a non-tumoral, untransformed phenotype, wherein the drug is doxorubicin, covalently bound through a spacer selected from bromobutanol or bromopropanol, with a substitution degree of doxorubicin at carboxyl of hyaluronic acid ranging from 3 to 20%.

11. The pharmaceutical formulation according to claim 10, wherein said neoplastic pathology is one associated with a nuclear accumulation of β-catenin protein.

12. The pharmaceutical formulation according to claim 10, wherein said neoplastic pathology is one associated with the inactivation of the APC-GSK-3β protein complex.

13. The pharmaceutical formulation according to claim 10, wherein said neoplastic pathology is one associated with the increase of the S phase of tumoral cell life.

14. The pharmaceutical formulation according to claim 10, wherein said treatment is for treating a primary tumor and its metastasis.

15. The pharmaceutical formulation according to claim 10, wherein said bioconjugate is capable of differentiating tumoral cells associated with a nuclear accumulation of β-catenin protein and with the inactivation of the APC-GSK-3β protein complex towards a non-tumoral phenotype.

16. The pharmaceutical formulation according to claim 10, further comprising β-cyclodextrin or liposomes.

17. The pharmaceutical formulation according to claim 16, containing β-cyclodextrin at 1.5% w/v.

18. The pharmaceutical formulation according to claim 16, further comprising glucose.

19. The pharmaceutical formulation according to claim 18 in a solution of glucose at 5% w/v.

20. The method according to claim 1, wherein the substitution degree of doxorubicin at carboxyl of hyaluronic acid is 10%.

* * * * *